United States Patent
Gaines et al.

(10) Patent No.: US 10,624,675 B2
(45) Date of Patent: Apr. 21, 2020

(54) SPINAL STABILIZATION SYSTEM

(71) Applicant: K2M, INC., Leesburg, VA (US)

(72) Inventors: Robert Gaines, Columbia, MO (US); Kan Min, Zollikon (CH); Brandon Moore, Summit Point, WV (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 15/620,206

(22) Filed: Jun. 12, 2017

(65) Prior Publication Data

US 2017/0273719 A1 Sep. 28, 2017

Related U.S. Application Data

(63) Continuation of application No. 14/604,136, filed on Jan. 23, 2015, now Pat. No. 9,675,384.

(60) Provisional application No. 61/930,704, filed on Jan. 23, 2014.

(51) Int. Cl.
*A61B 17/70* (2006.01)
*A61B 17/80* (2006.01)

(52) U.S. Cl.
CPC ...... *A61B 17/7001* (2013.01); *A61B 17/7007* (2013.01); *A61B 17/7032* (2013.01); *A61B 17/7037* (2013.01); *A61B 17/7041* (2013.01); *A61B 17/7044* (2013.01); *A61B 17/809* (2013.01)

(58) Field of Classification Search
CPC .. A61B 17/7001; A61B 17/7035–7037; A61B 17/7041–7044; A61B 17/8038
See application file for complete search history.

(56) References Cited

U.S. PATENT DOCUMENTS

| | | | | |
|---|---|---|---|---|
| 5,681,311 A | * | 10/1997 | Foley | A61B 17/7059 606/283 |
| 5,704,936 A | * | 1/1998 | Mazel | A61B 17/7044 606/254 |
| 5,713,900 A | * | 2/1998 | Benzel | A61B 17/7059 606/250 |
| 6,945,972 B2 | * | 9/2005 | Frigg | A61B 17/7041 606/256 |
| 7,803,174 B2 | * | 9/2010 | Denis | A61B 17/7035 606/250 |
| 8,672,978 B2 | * | 3/2014 | Dant | A61B 17/7007 606/250 |
| 9,987,057 B2 | * | 6/2018 | Lawson | A61B 17/8894 |

(Continued)

*Primary Examiner* — Jacqueline T Johanas
(74) *Attorney, Agent, or Firm* — Lerner, David, Littenberg, Krumholz & Mentlik, LLP (57) ABSTRACT

A spinal stabilization system includes a spinal rod, a plate, a set screw, and a bone screw. The plate includes a through-hole transitionable between a collapsed and expanded configuration, and a first slot adapted to receive a spinal rod therein. The set screw includes a distal portion having threads to engage with a threaded lumen of a bone screw, and the bone screw including a head portion transitionable between a first diameter and a second diameter. The head of the bone screw insertable into the throughhole and cooperatively transitions between the first diameter and the collapsed configuration to the second diameter and expanded configuration, respectively, as the set screw advances with respect to the bone screw to lock the spinal rod into the slot of the plate in the second diameter and expanded configuration.

19 Claims, 11 Drawing Sheets

(56) References Cited

U.S. PATENT DOCUMENTS

| | | | |
|---|---|---|---|
| 2004/0147928 A1* | 7/2004 | Landry | A61B 17/1655 606/86 A |
| 2005/0070901 A1 | 3/2005 | David | |
| 2005/0182409 A1* | 8/2005 | Callahan | A61B 17/7007 606/308 |
| 2005/0228382 A1 | 10/2005 | Richelsoph et al. | |
| 2005/0251141 A1 | 11/2005 | Frigg et al. | |
| 2005/0277931 A1* | 12/2005 | Sweeney | A61B 17/1671 606/264 |
| 2006/0116676 A1* | 6/2006 | Gradel | A61B 17/7041 606/278 |
| 2007/0123860 A1* | 5/2007 | Francis | A61B 17/7035 606/250 |
| 2007/0173827 A1* | 7/2007 | Morrison | A61B 17/7037 606/86 A |
| 2007/0233062 A1* | 10/2007 | Berry | A61B 17/7004 606/914 |
| 2008/0208257 A1 | 8/2008 | Matthys | |
| 2008/0312692 A1* | 12/2008 | Brennan | A61B 17/7005 606/246 |
| 2009/0012571 A1* | 1/2009 | Perrow | A61B 17/1671 606/280 |
| 2009/0062860 A1* | 3/2009 | Frasier | A61B 17/701 606/278 |
| 2009/0270927 A1* | 10/2009 | Perrow | A61B 17/7059 606/286 |
| 2010/0094358 A1* | 4/2010 | Moore | A61B 17/0642 606/319 |
| 2010/0198260 A1* | 8/2010 | Gabelberger | A61B 17/7037 606/264 |
| 2010/0211116 A1* | 8/2010 | Suh | A61B 17/8033 606/305 |
| 2010/0222822 A1 | 9/2010 | Farris et al. | |
| 2010/0268279 A1 | 10/2010 | Gabelberger et al. | |
| 2010/0331897 A1* | 12/2010 | Lindner | A61B 17/7041 606/305 |
| 2011/0004251 A1* | 1/2011 | Sweeney | A61B 17/1671 606/264 |
| 2012/0226316 A1* | 9/2012 | Dant | A61B 17/7007 606/250 |
| 2012/0303062 A1 | 11/2012 | Amstutz et al. | |
| 2013/0072991 A1 | 3/2013 | Rathbun | |
| 2013/0338715 A1 | 12/2013 | Daly et al. | |
| 2013/0345755 A1* | 12/2013 | Prajapati | A61B 17/7007 606/273 |
| 2014/0135928 A1* | 5/2014 | Sweeney | A61B 17/1671 623/17.12 |
| 2014/0296925 A1* | 10/2014 | Lawson | A61B 17/8033 606/289 |

* cited by examiner

SPINAL STABILIZATION SYSTEM

CROSS-REFERENCE TO RELATED APPLICATIONS

The present application is a continuation of U.S. patent application Ser. No. 14/604,136, filed on Jan. 23, 2015, which claims the benefit of and priority to U.S. Provisional Application Ser. No. 61/930,704, filed on Jan. 23, 2014, the entire contents of each of which are incorporated herein by reference.

BACKGROUND

Technical Field

The present disclosure relates to an orthopedic surgery system for stabilizing and fixing the bones and joints of the body. Particularly, the present disclosure relates to a spinal stabilization system including a spinal rod, bone screws, set screws, and plates. Alternatively, the spinal stabilization system may include bone screws, threaded nuts, and a plate.

Description of Related Art

The spinal column is a complex system of bones and connective tissues that provides support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending, and rotational loads and motions.

There are various disorders, diseases, and types of injury that the spinal column may experience in a lifetime. The problems may include but are not limited to scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis or bone tissue thinning and loss of bone density. Spinal discs between the endplates of adjacent vertebrae in a spinal column of the human body provide critical support. However, due to injury, degradation, disease or the like, these discs can rupture, degenerate and/or protrude to such a degree that the intervertebral space between adjacent vertebrae collapses as the disc loses at least a part of its support function. This can cause impingement of the nerve roots and severe pain.

One of the more common solutions to any of the above mentioned conditions involves a surgical procedure known as spinal fusion. A spinal fusion procedure involves fusing two or more vertebral bodies in order to stabilize or eliminate motion at the intervertebral disc or joint. To achieve this, natural or artificial bone, along with a spacing device, replaces either part, or the entire intervertebral disc to form a rigid column of bone, which is stabilized by implantable mechanical hardware.

The mechanical hardware used to immobilize the spinal column typically involves a series of bone screws/anchors and metal rods and/or plates. When the spine surgery is performed posteriorly, it is common practice to place bone screws into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

However, as in the case of all spinal corrective surgery, a significant amount of instrumentation may still be required to perform the bone on bone technique. The process of properly inserting the spinal rod into the receiving slot of a bone screw and then securing that connecting rod in place can often require that the clinician use a number of instruments and expend a great deal of time and effort. This instrumentation will remain permanently attached to the patient's spinal column throughout the patient's lifetime posing potential risks to the patient's long term health. Therefore, a need exits for an implantable device that provides support and remains in place during use, but maintains a low profile. The implantable devices disclosed herein address one or more deficiencies in the art.

SUMMARY

The present disclosure is directed to a spinal stabilization system including a first spinal rod, a bone screw, a plate, and a set screw. The bone screw includes a head portion and a threaded distal portion extending therefrom. The head portion is transitionable between a first diameter and a second diameter. The plate includes a throughhole and a first slot, wherein the first slot is transverse to an axis extending through the throughhole. The throughhole is transitionable between a collapsed configuration and an expanded configuration, such that a diameter of the throughhole in the expanded configuration is greater than the diameter of the throughhole in the collapsed configuration. The set screw includes a head portion adapted to receive a driving tool and a distal portion extending therefrom. The distal portion has threads for engaging a threaded lumen of the bone screw, and the head portion of the bone screw is insertable into the throughhole. Rotation of the set screw relative to the bone screw advances the set screw and transitions the head portion of the bone screw towards the second diameter, and transitions the throughhole towards the expanded configuration, such that a diameter of the first slot decreases for securing the first spinal rod in the first slot.

In an embodiment of the present disclosure, the head portion of the bone screw further includes a plurality of longitudinally extending segments radially disposed about a longitudinal axis of the bone screw. The plurality of longitudinally extending segments are flexibly transitionable between the first and second diameters of the head portion. In another embodiment, the plurality of longitudinally extending segments of the bone screw are biased radially inward.

In an embodiment of the present disclosure, the plate further includes a plurality of flexible segments radially disposed about the diameter of the throughhole. The plurality of flexible segments are transitionable between the collapsed and expanded configurations. In another embodiment, the plurality of flexible segments of the plate are biased towards the collapsed configuration.

In an embodiment of the present disclosure, the plate further includes a bone spike disposed on a distal surface thereof adapted to penetrate bone. In another embodiment, the distal surface of the plate is arcuate.

In another embodiment of the present disclosure, the spinal stabilization system further includes a second spinal rod and a second slot on the plate, the second slot transverse to the axis extending through the throughhole. A diameter of the second slot decreases when the throughhole transitions towards the expanded configuration, thereby securing the second spinal rod in the second slot of the plate.

In another aspect of the present disclosure, a method of stabilizing a spine includes, providing a first spinal rod, a bone screw, a plate, and a set screw. The bone screw includes a head portion and a threaded distal portion extending therefrom, the head portion transitionable between a first diameter and a second diameter. The plate includes a throughhole and a first slot, the first slot transverse to an axis extending through the throughhole, and the throughhole is transitionable between a collapsed configuration and an expanded configuration. The set screw includes a head portion adapted to receive a driving tool and a distal portion extending therefrom, the distal portion having threads for engaging a threaded lumen of the bone screw. The head portion of the bone screw is insertable into the throughhole such that rotation of the set screw relative to the bone screw advances the set screw and transitions the head portion of the bone screw towards the second diameter, and transitions the throughhole towards the expanded configuration, such that a diameter of the first slot decreases securing the first spinal rod into the first slot. The method further includes implanting the bone screw into a bone of a patient, positioning the head portion of the bone screw into the throughhole of the plate, adjusting the contour of the first spinal rod as need, and placing the first spinal rod into the first slot. The method also includes engaging the threads of the set screw to the threaded lumen of the bone screw, and advancing the set screw with respect to the bone screw with a driving tool such that the diameter of the first slot is reduced.

In an embodiment of the present disclosure, the method further includes, providing a second spinal rod and a second slot on the plate. The second slot is transverse to the axis extending through the throughhole, and with the throughhole in the expanded configuration, a diameter of the second slot is decreased thereby securing the second spinal rod into the second slot. The method further includes, adjusting the contour of the second spinal rod as needed, and placing the second spinal rod into the second slot, wherein advancing the set screw with respect to the bone screw secures the second spinal rod in the second slots.

In an embodiment of the present disclosure, the method may further include, incrementally advancing the set screw, and realigning the spinal rod throughout the advancement of the set screw.

In another embodiment of the present disclosure, the method may further include, providing a plurality of bone screws, and a plurality of plates. The method may include, implanting the plurality of bone screws in sequence to bones of a patient, and coupling the plurality of plates to the plurality of bone screws implanted into bone. The first spinal rod is then secured within the first slot of each plate of the plurality of plates coupled to the plurality of bone screws, such that the first spinal rod spans multiple bones.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION OF EMBODIMENTS

Embodiments of the present disclosure are now described in detail with reference to the drawings in which like reference numerals designate identical or corresponding elements in each of the several views. As is understood in the art, the term "clinician" refers to a doctor, a nurse, or any other care provider and may include support personnel. Throughout this description, the term "proximal" will refer to the portion of the apparatus or component thereof that is closer to the clinician and the term "distal" will refer to the portion of the apparatus or component thereof that is farther from the clinician. In addition, the term "cephalad" is used in this application to indicate a direction toward a patient's head, whereas the term "caudad" indicates a direction toward the patient's feet. Further still, for the purposes of this application, the term "lateral" indicates a direction toward a side of the body of the patient, i.e., away from the middle of the body of the patient, whereas "medial" refers to a position toward the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure.

Figure 1:
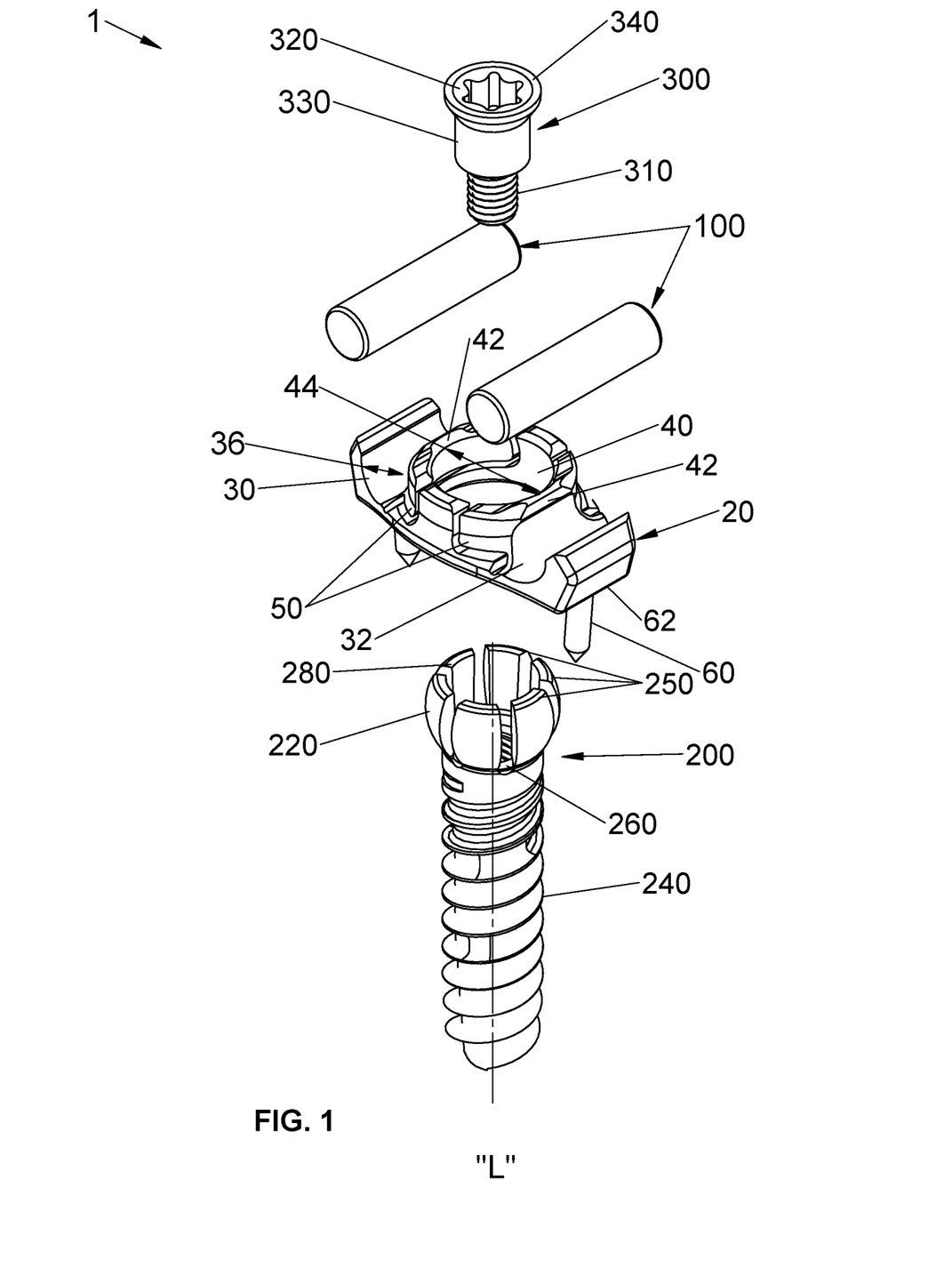
FIG. 1 is a front perspective view, with parts separated, of one embodiment of a spinal stabilization system in accordance with the present disclosure.
Figure 2:
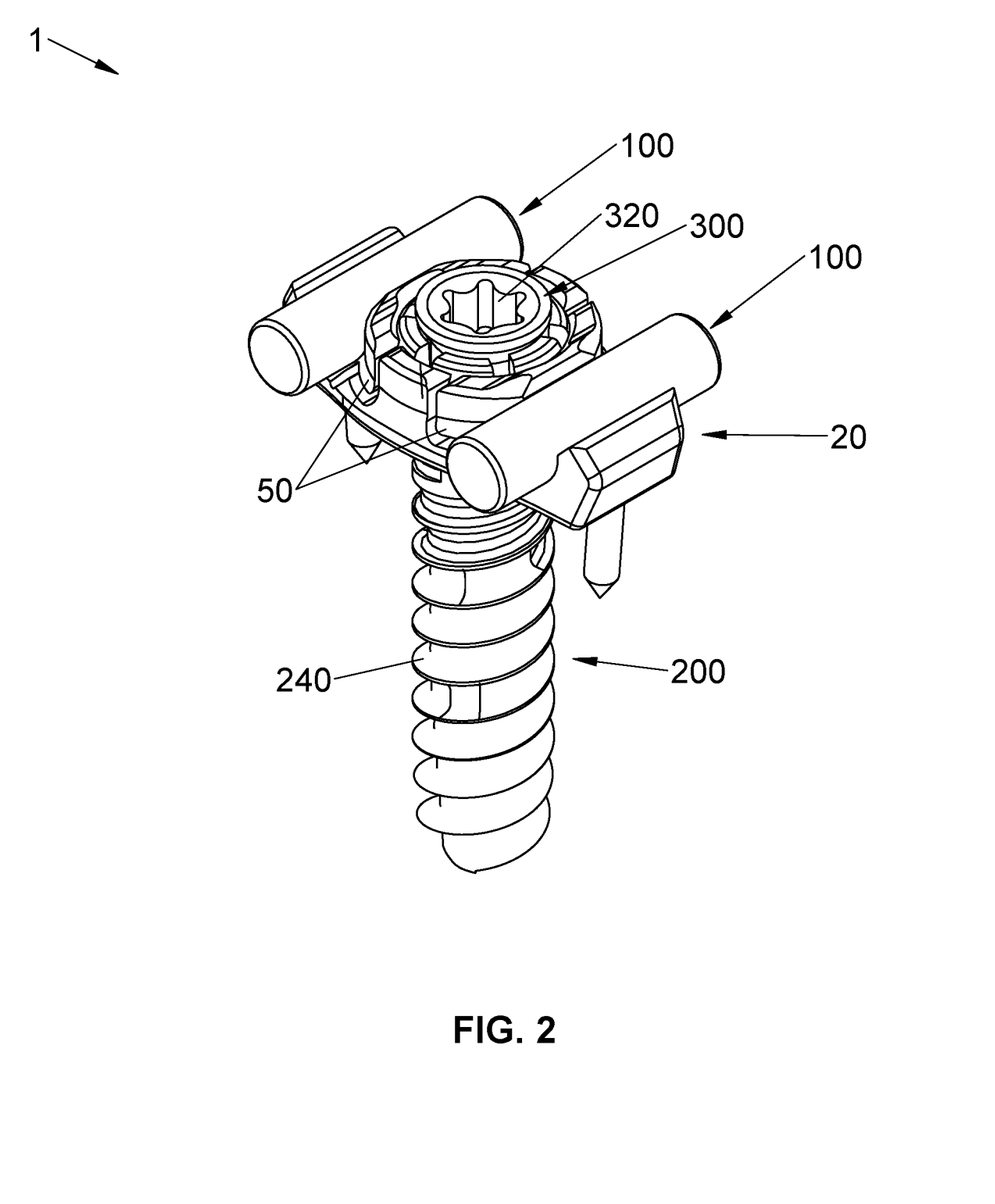
FIG. 2 is a front perspective view of the spinal stabilization system of FIG. 1 with parts assembled.
Figure 6:
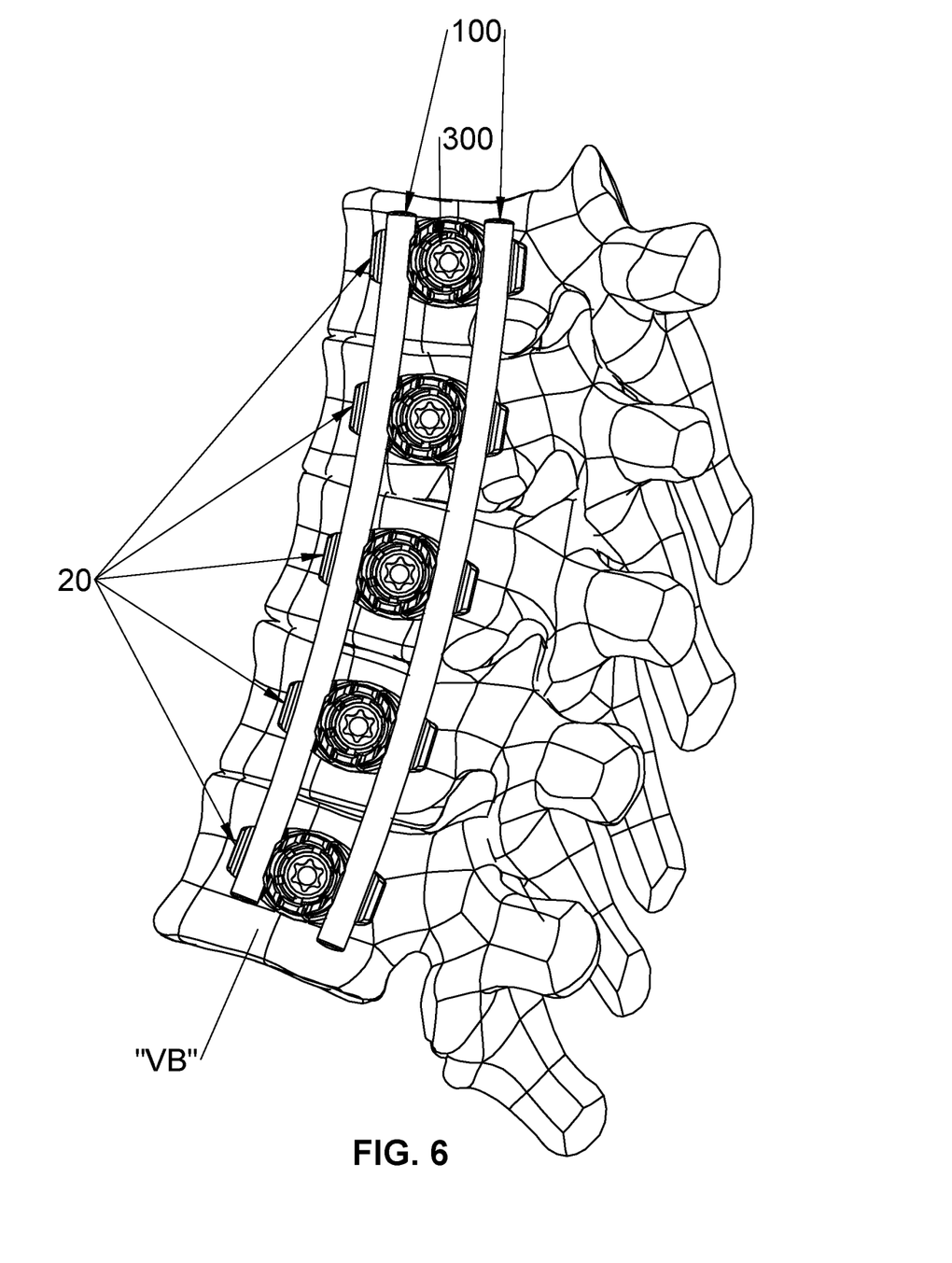
FIG. 6 is a top view of a construct using the spinal stabilization system of FIG. 1.

With initial reference to FIGS. 1 and 2, an embodiment of a spinal stabilization system 1 will be generally described. Spinal stabilization system 1 includes a plate 20, a spinal rod 100, a bone screw 200, and a set screw 300. It is envisioned that spinal stabilization system 1 may further include a plurality of spinal rods 100 such that a two-rail construct is assembled (FIG. 2). Additionally, spinal stabilization system 1 may include a plurality of plates 20, a plurality of spinal rods 100, a plurality of bone screws 200, and a plurality of set screw 300, such that spinal stabilization system 1 sequentially spans across a plurality of vertebral bodies "VB" (FIG. 6). Spinal stabilization system 1 has a low profile of about 3 mm to about 4 mm in height. Providing a low profile spinal stabilization system 1 may allow the surgeon to easily close the surgical site reducing pain to the patient and minimizing irritation and damage to the surround tissue, muscle, and organs.

Figure 4A:
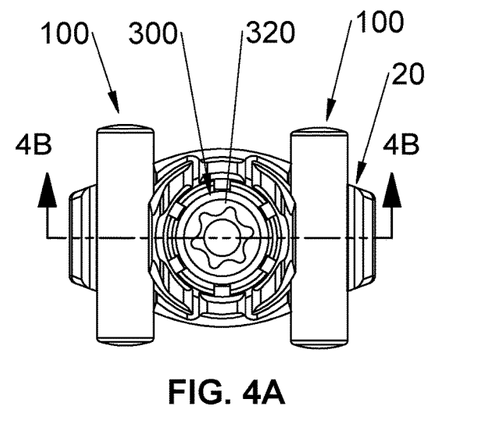
FIG. 4A is a top view of the spinal stabilization system of FIG. 2 in the unlocked configuration.
Figures 4B, 5B:
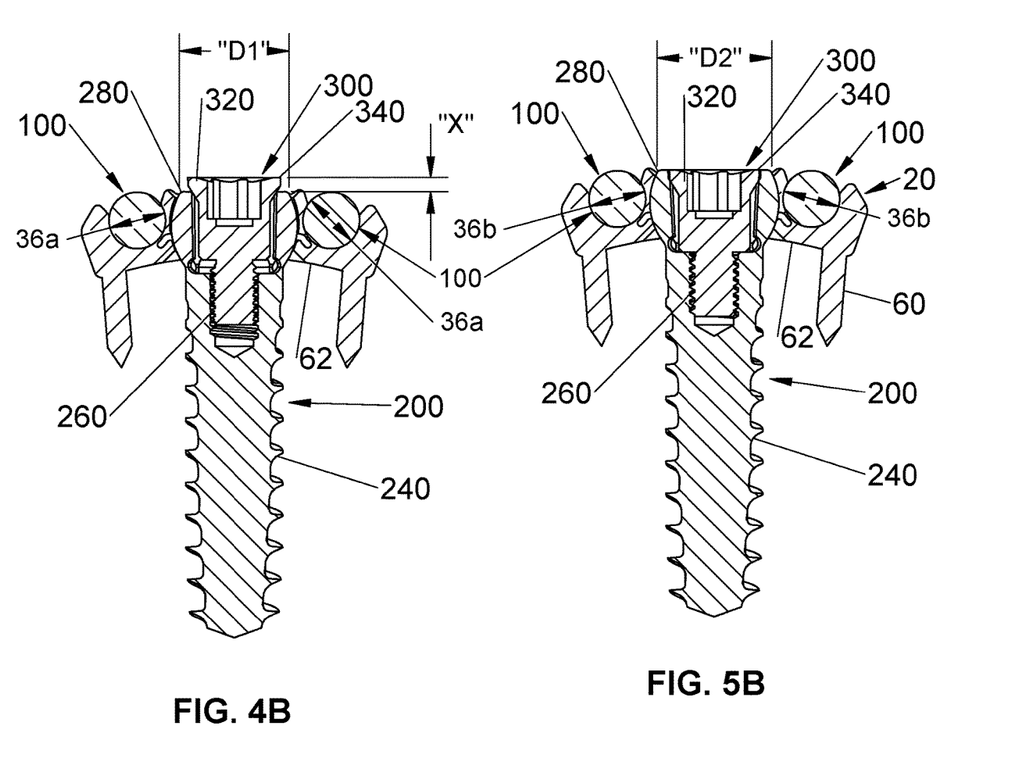
FIG. 4B is a cross-sectional view taken along section line 4B-4B of FIG. 4A.
FIG. 5B is a cross-sectional view taken along section line 5B-5B of FIG. 5A.
Figure 5A:
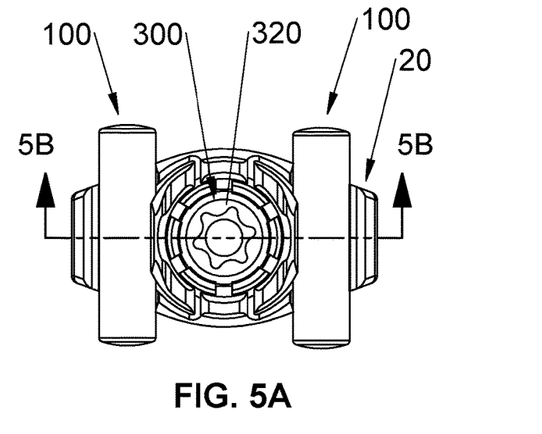
FIG. 5A is a top view of the spinal stabilization system of FIG. 2 in the locked configuration.

Plate 20 includes a throughhole 40, a first slot 30, and a second slot 32, wherein first and second slots 30, 32 are on opposite sides of, and transverse to, throughhole 40. Each slot 30, 32 has a diameter 36. Although shown with two slots 30, 32, it is contemplated that plate 20 may only include a single slot 30 or 32. Throughhole 40 includes a plurality of slotted wall segments 50 that are transitionable between a collapsed configuration (FIG. 4B) and an expanded configuration (FIG. 5B). Additionally, throughhole has a diameter 44 which is dimensioned to receive bone screw 200 therethrough. In the collapsed configuration, diameter 44 of throughhole 40 is less than the diameter 44 of throughhole 40 in the expanded configuration. As diameter 44 of throughhole 40 increases, shoulders 42 of throughhole 40 urge first and second slots 30, 32 to transition from an initial diameter 36a (FIG. 4B) to a reduced diameter 36b (FIG. 5B), as described more fully below.

Each of the first and second slots 30, 32 of plate 20 are adapted to receive a respective spinal rod 100 therein. With throughhole 40 in the collapsed configuration, first and second slots 30, 32 have the initial diameter 36a, dimensioned such that first and second slot 30, 32 may receive a spinal rod 100 therein. It is envisioned that spinal rod 100 may have a diameter between about 3 mm and about 8 mm. Further, that the diameter, shape, and material of spinal rod 100 may be chosen based on the requirements of the surgical procedure and the desired mechanical characteristics of spinal rod 100, e.g., rigidity, flexural modulus, flexural strength, plasticity, yield strength, etc. It should be appreciated that with throughhole 40 in the expanded configuration, first and second slots 30, 32 transition to the reduced diameter 36b, such that the shoulders 42 of throughhole 40 comes into contact with a portion of spinal rod 100, exerting a compressive force thereon and securing spinal rod 100 within a respective first and second slots 30, 32.

Figure 3:
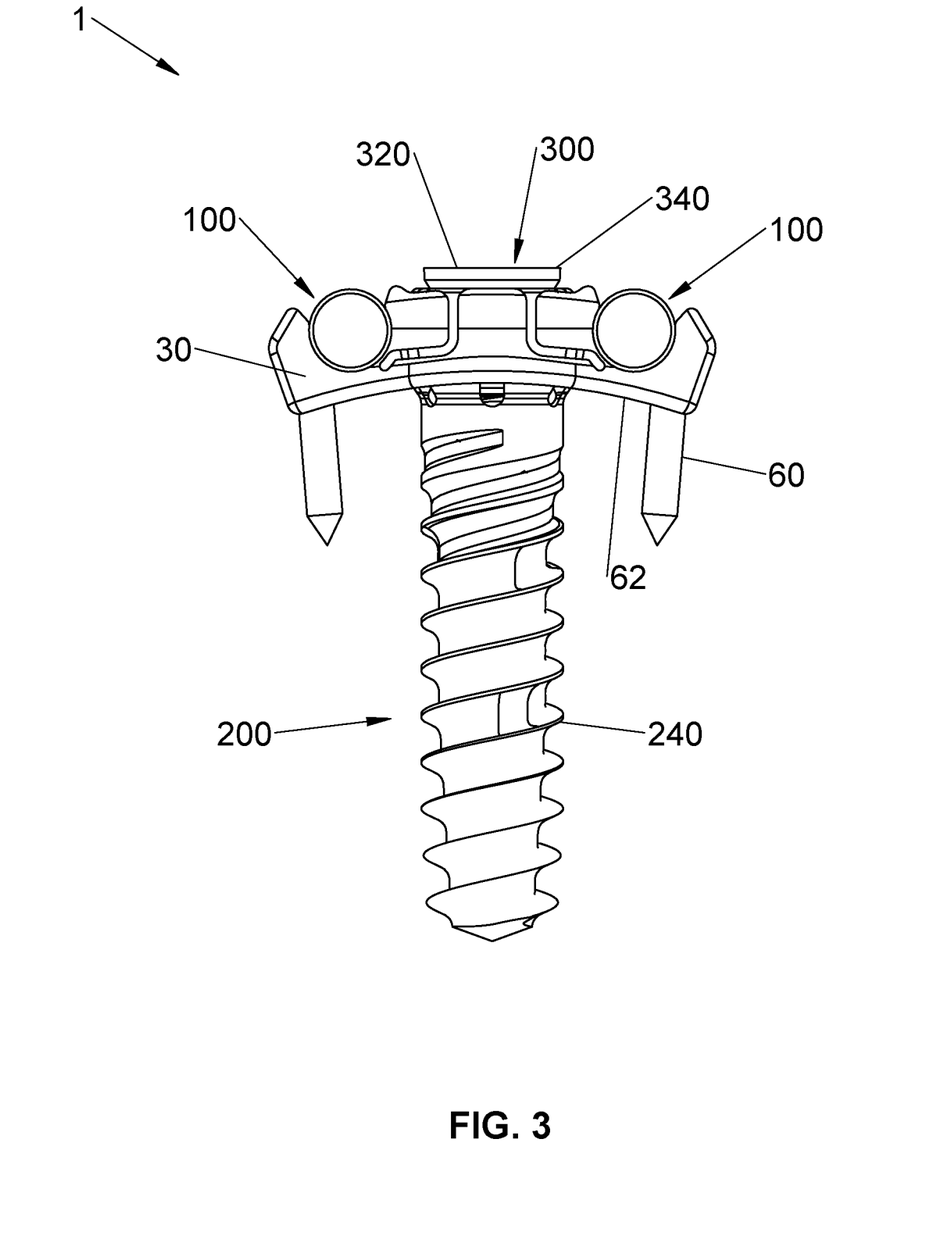
FIG. 3 is an end view of the spinal stabilization system of FIG. 2.

It is further envisioned that plate 20 may include one or more bone spikes 60 extending from a distal surface 62 (FIG. 3). Additionally, distal surface 62 may further define an arcuate surface such that plate 20 may be set flush against vertebral body "VB". Bone spike 60 is adapted to penetrate the vertebral body "VB" such that plate 20 may be initially positioned and fixed with respect to the vertebral body "VB". Once plate 20 is positioned in a desired location, bone spikes 60 are driven into the vertebral body "VB", such that plate 20 will be resistant to twisting, sliding, or other movement during the construction of spinal stabilization system 1.

With continued reference to FIG. 1, bone screw 200 includes a head portion 220 and a threaded portion 240 extending distally therefrom. Threaded portion 240 has a smaller outer diameter than head portion 220 and is configured to secure bone screw 200 to bone, such as a vertebral body "VB". Head portion 220 may further include a plurality of longitudinally extending segments 250 that are radially disposed about a longitudinal axis "L" of bone screw 200. Bone screw 200 further includes a threaded lumen 260 (FIGS. 4B and 5B) adapted to receive a threaded portion 310 of set screw 300 (discussed below).

Head portion 220 of bone screw 200 is biased towards a first diameter "$D_1$" (FIG. 4B) and is transitionable to a second diameter "$D_2$" (FIG. 5B) such that the second diameter "$D_2$" is greater than the first diameter "$D_1$". When bone screw 200 is coupled to plate 20, first diameter "$D_1$" and second diameter "$D_2$" of head portion 220 correspond to the collapsed and expanded configurations, respectively, of throughhole 40. It should be appreciated that when head portion 220 has the first diameter "$D_1$", throughhole 40 is in the collapsed configuration, and when head portion 220 is expanded to the second diameter "$D_2$", throughhole 40 transitions to the expanded configuration. Thus, the transition of head portion 220 and throughhole 40 cooperatively act to simultaneously transition the slots 30, 32 from the initial diameter 36a to the reduced diameter 36b.

Set screw 300 includes a head portion 320, a body portion 330, and a threaded portion 310 extending distally from body portion 330. It is envisioned that head portion 320 may be adapted to receive a driving tool (not shown), e.g., hex head, Philips head, slotted driver, etc. Set screw 300 is dimensioned such that it is received within head portion 220 of bone screw 200. When threaded portion 310 of set screw 300 is initially coupled with the threaded lumen 260 of bone screw 200, the body portion 330 of set screw 300 is disposed within the head portion 220 of bone screw 200 (FIG. 4B). In this initial position, head portion 320 of set screw 300 is spaced away from and proximal of head portion 220 of bone screw 200, such that a distance "X" is defined between a proximal surface 340 of set screw 300 and a proximal surface 280 of bone screw 200. Once the threaded portion 310 of set screw 300 is fully coupled with the threaded lumen 260 of bone screw 200, the body portion 330 is fully disposed within the head portion 220 of bone screw 200. With set screw 300 fully coupled to bone screw 200, the head portion 320 of set screw 300 may also be disposed within the head portion 220 of bone screw 200 and/or the proximal surface 340 of set screw 300 may be substantially flush with the proximal surface 280 of bone screw 200 (FIG. 5B).

It should be appreciated that set screw 300, bone screw 200, and plate 20 act cooperatively to secure and lock spinal rod 100 in a respective first or second slot 30, 32 of plate 20. Plate 20 may initially maintain an unlocked position wherein set screw 300 is not fully engaged with bone screw 200, head portion 220 of bone screw 200 has the first diameter "$D_1$", throughhole 40 is in the collapsed configuration, and the first and second slots 30, 32 have initial diameter 36a. Plate 20 is transitioned into a locked position wherein set screw 300 is advanced with respect to the longitudinal axis "L" of bone screw 200, such that head portion 320 of set screw 300 imparts a radial force against the head portion 220 of bone screw 200, resulting in a radial force against slotted wall segments 50 of throughhole 40. This transitions the throughhole 40 from the collapsed configuration to the expanded configuration thereby causing shoulders 42 to reduce the diameter of slots 30, 32 into the reduced diameter 36b.

More specifically, as set screw 300 is advanced with respect to bone screw 200, the radially inward bias of head portion 220 of bone screw 200 is overcome to effect the transition of throughhole 40 into the expanded configuration. As throughhole 40 is transitioned to the expanded configuration, each of the first and second slots 30, 32 transition from the initial diameter 36a to the reduced diameter 36b resulting in a compressive force upon the portion of spinal rod 100 disposed therein. Further, through incremental advancement of set screw 300 with respect to bone screw 200, the initial diameter 36a of first and second slots 30, 32 may be incrementally reduced to the reduced diameter 36b, such that the compressive force upon spinal rod 100 is gradually applied. As a result, spinal rod 100 may be initially or loosely secured within a respective first or second slot 30, 32 permitting adjustment and realignment of spinal rod 100 and spinal stabilization system 1. Set screw 300 can then be completely advanced with respect to bone screw 200 to fully secure spinal rod 100 within a respective first or second slot 30, 32.

With reference to FIGS. 7-12, an alternate embodiment of spinal stabilization system 1 will be described with reference to spinal stabilization system 500. Spinal stabilization system 500 includes a plate 520, a bone screw 600, and a threaded nut 700. It is envisioned that spinal stabilization system 500 may include a plurality of bone screws 600 and threaded nuts 700.

Figure 7:
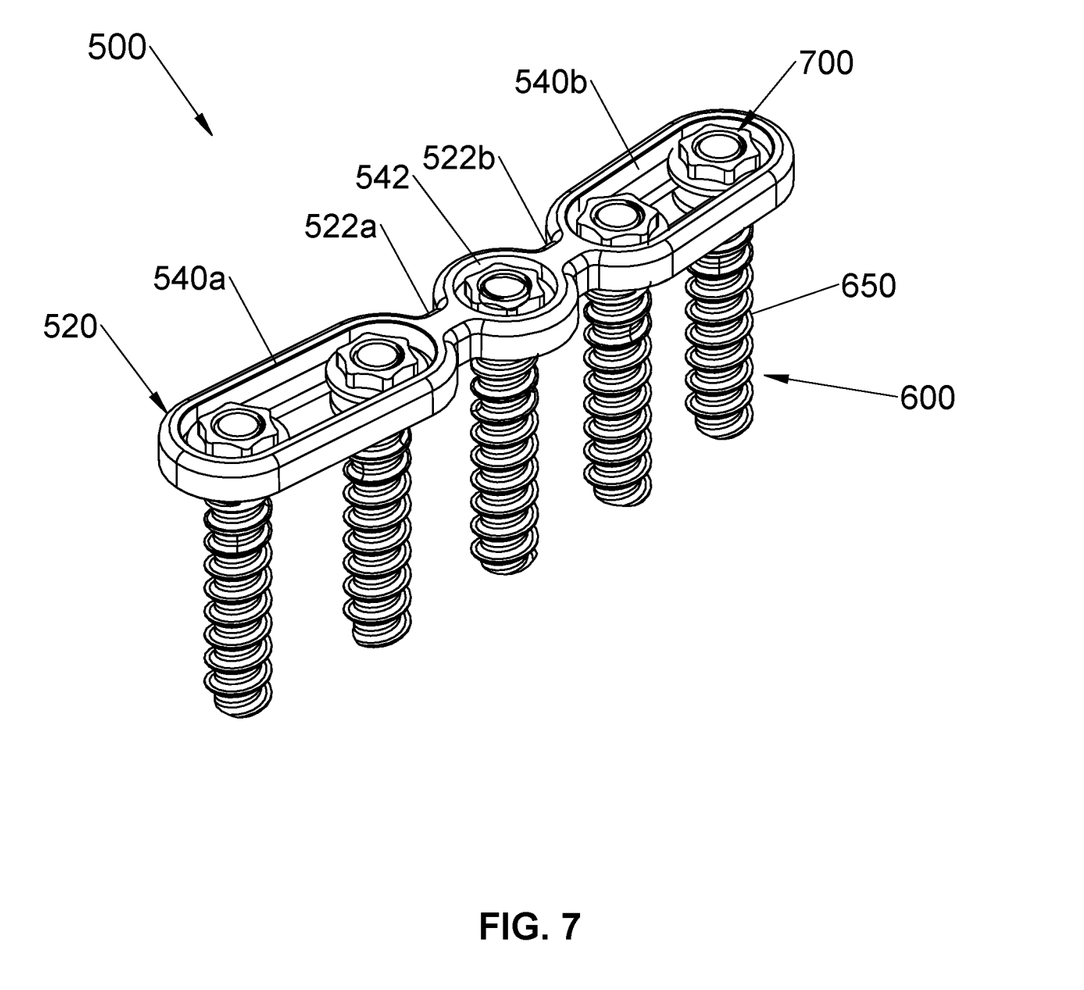
FIG. 7 is a top perspective view of another embodiment of the spinal stabilization system in accordance with the present disclosure.
Figure 8:
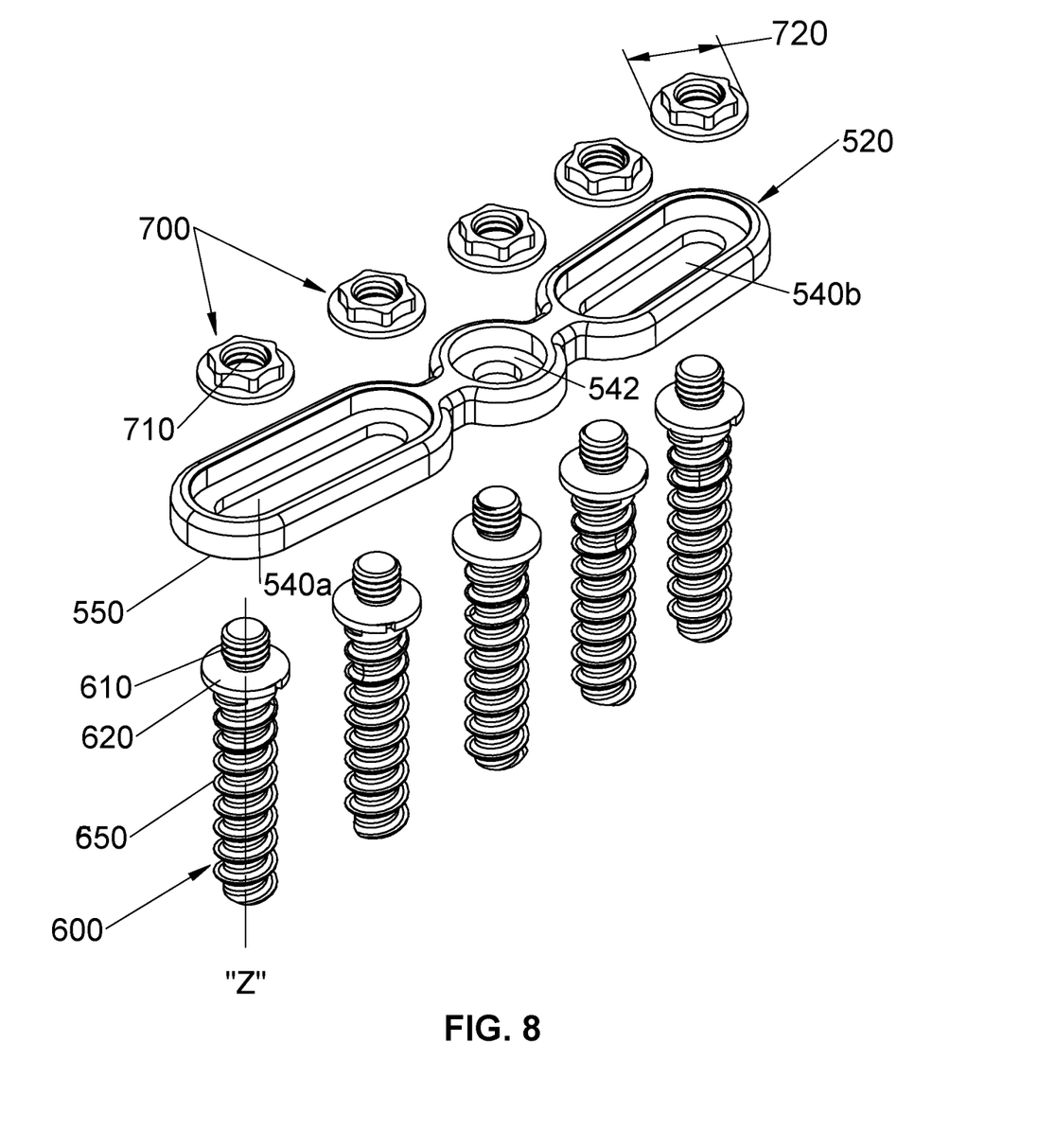
FIG. 8 is a top perspective view, with parts separated, of the spinal stabilization system of FIG. 7.

With initial reference to FIGS. 7 and 8, plate 520 includes a throughhole 542, a neck portion 522a, 522b extending from opposing sides of throughhole 542, and an elongated slot 540a, 540b extending from each respective neck portion 522a, 522b. It is envisioned that plate 520 may alternatively include a single elongated slot or a plurality of elongated slots disposed along a length (not shown) of plate 520. Further, plate 520 may include a plurality of throughholes 542 disposed along the length of plate 520.

Figure 9:
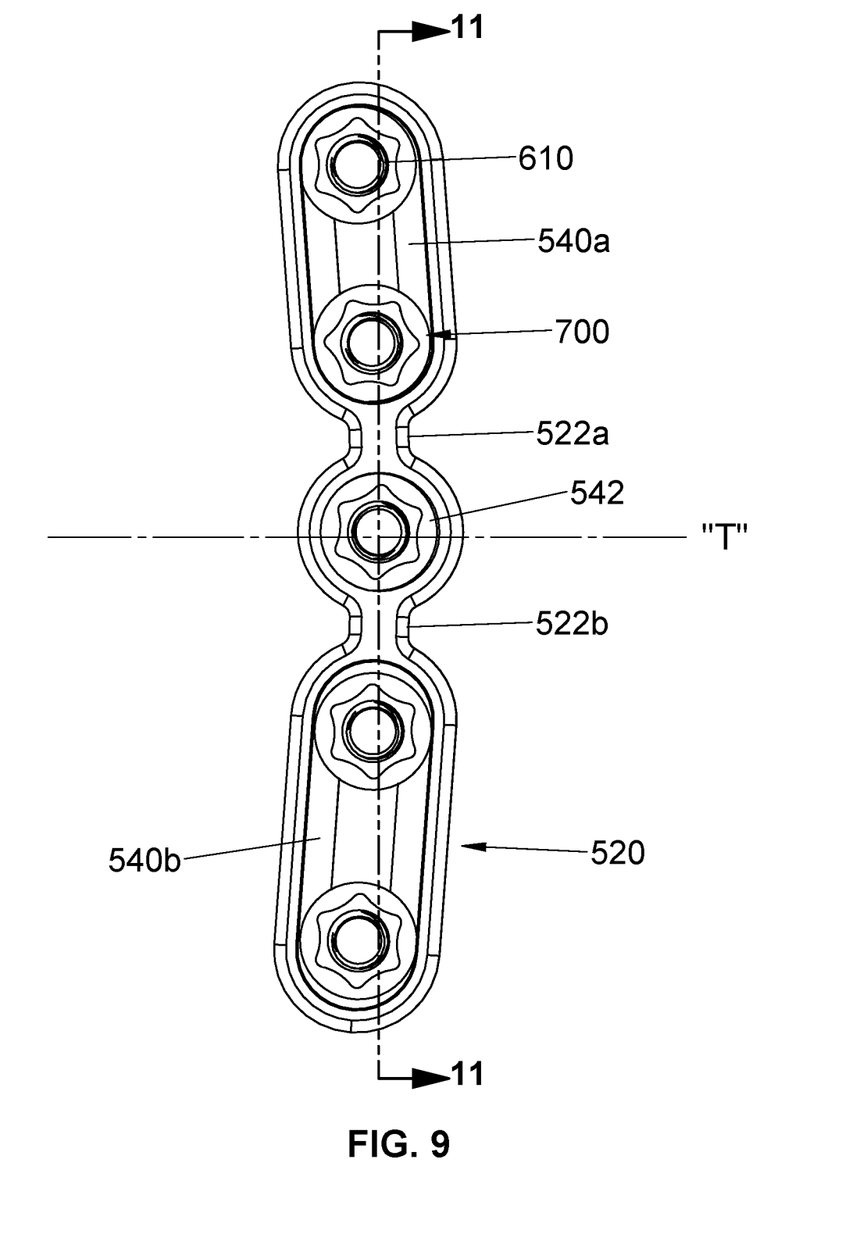
FIG. 9 is a top view of the spinal stabilization system of FIG. 7.
Figure 10:
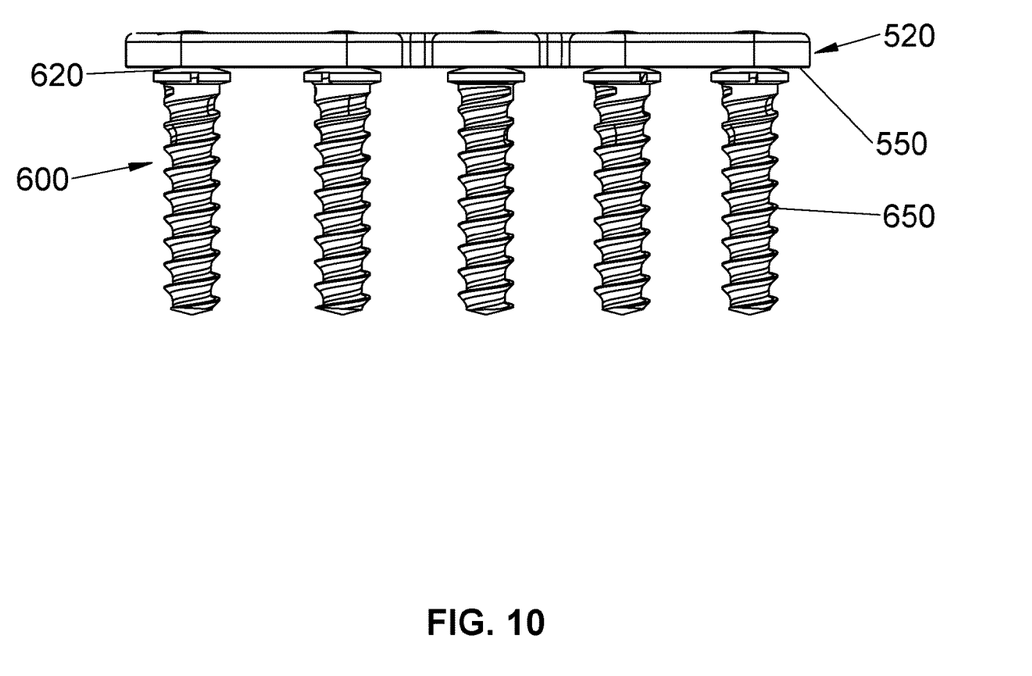
FIG. 10 is a side view of the spinal stabilization system of FIG. 7.

As illustrated in FIG. 9, it is envisioned that the length of plate 520 may be generally arcuate. Additionally, elongated slot 540a may be symmetrical to elongated slot 540b about an axis "T" being transverse to throughhole 542. Further, it is envisioned that a length of elongated slot 540a may be generally similar to a length of elongated slot 540b, or the length of elongated slot 540a may differ from the length of elongated slot 540b.

Figure 11:
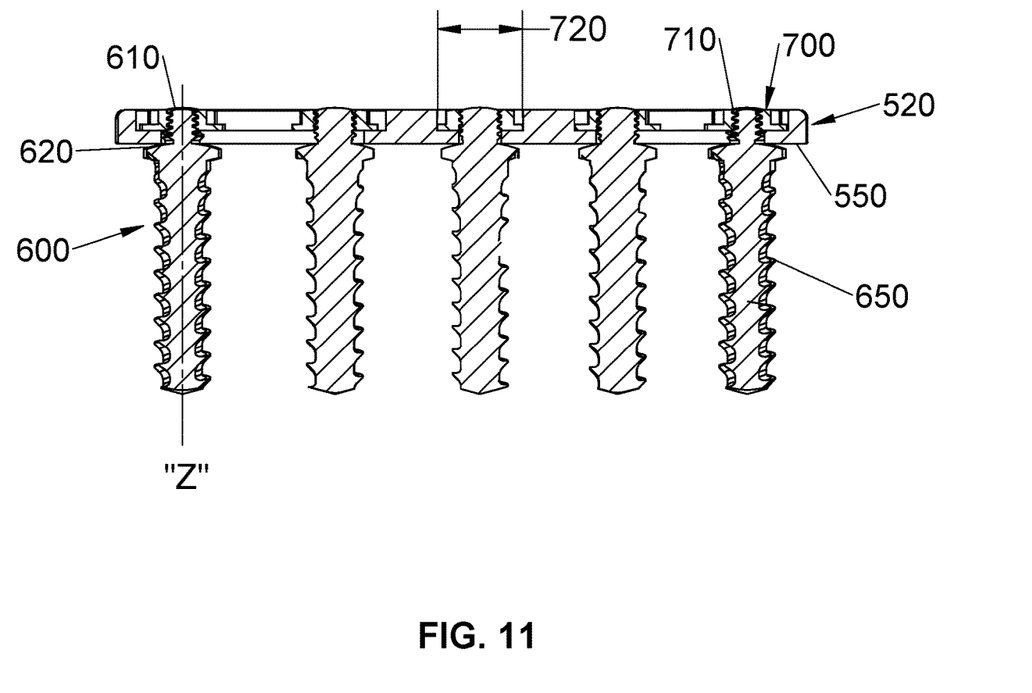
FIG. 11 is a side cross-sectional view taken along section line 11-11 of FIG. 9.
Figure 12:
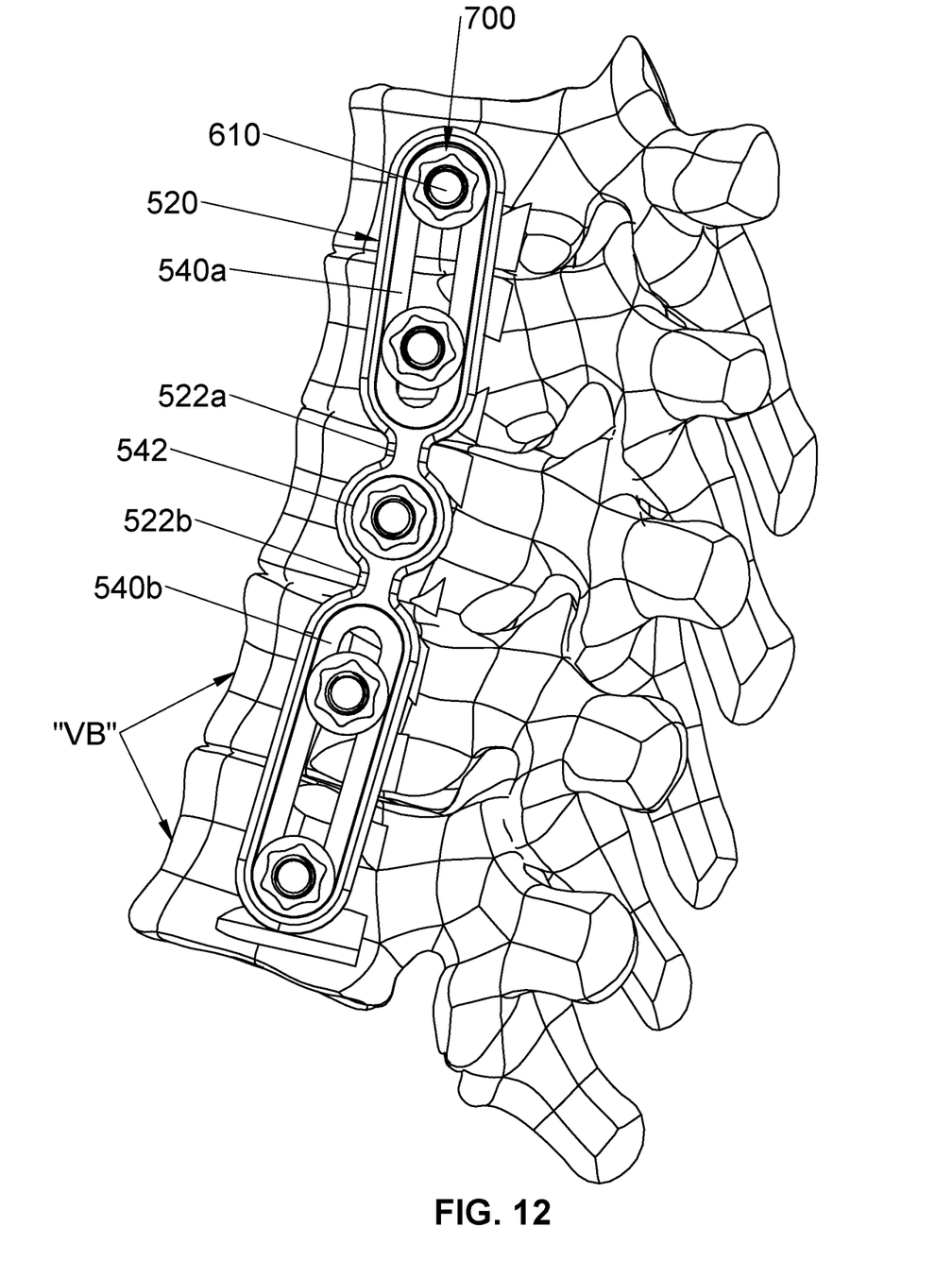
FIG. 12 is a top view of a construct using the spinal stabilization system of FIG. 7.

With reference to FIGS. 8 and 11, bone screw 600 includes a threaded post 610 and a threaded portion 650 extending distally therefrom. Threaded portion 650 is adapted to secure bone screw 600 to bone, such as a vertebral body "VB". Threaded post 610 further includes a seat 620 such that when plate 520 is positioned over bone screw 600, with threaded post 610 extending through one of elongated slots 540a, 540b, a distal surface 550 of plate 520 abuts seat 620.

Threaded nut 700 includes a threaded inner surface 710 adapted to engage with the threaded post 610 of bone screw 600. Threaded nut 700 is rotated with respect to a longitudinal axis "Z" of bone screw 600, such that plate 520 is disposed between threaded nut 700 and seat 620 of bone screw 600. Once threaded nut 700 is fully advanced, plate 520 is fully secured between the threaded nut 700 and bone screw 600. Threaded nut 700 further includes an outer diameter 720 dimensioned to fit within a respective elongated slot 540a, 540b when coupled to threaded post 610 of bone screw 600, such that threaded nut 700 is fully disposed within the respective elongated slot 540a, 540b. It should be appreciated that threaded nut 700 and threaded post 610 of bone screw 600 interact similarly with throughhole 542, such that when threaded nut 700 is coupled to threaded post 610, threaded nut 700 is fully disposed within throughhole 542.

A method of stabilizing a spine in accordance with the present disclosure using spinal stabilization system 1 will now be described with reference to FIGS. 1-6. A clinician may initially stretch a patient's spine by pulling on the head and feet of the patient while imaging their spine. This allows the clinician to see the segments of the spine that can easily be corrected and pin point the segments where a discectomy or spinal repair is need to be performed. This allows for the clinician to operate on fewer segments of the spine and thus allow for less morbidity to the patient. It is these few segments that will be mated together in a bone on bone construct to allow fusion and the insertion of a plate member on one lateral side of the vertebral bodies "VB" to aid in stabilizing the spine. Generally, once the discectomies are complete a spinal stabilization construct is assembled.

The clinician is provided with spinal rod 100, bone screw 200, set screw 300, and plate 20. Initially, the clinician may pre-drill a hole and/or directly implant bone screw 200 into the vertebral body "VB" by using a driving tool to secure threaded portion 240 of bone screw 200 into the vertebral body "VB". Bone screw 200 is implanted such that head portion 220 is disposed above, and proximal to, vertebral body "VB". Plate 20 is next coupled to the head portion 220 of bone screw 200, such that head portion 220 is disposed within throughhole 40 of plate 20. Alternatively, the clinician may first position plate 20 onto the vertebral body "VB", such that the distal surface 62 abuts the vertebral body "VB" and the bone spikes 60 are driven into the vertebral body "VB" to hold plate 20 in an initial position. It is contemplated that a suitable driving tool (e.g., hammer, mallet, etc.) as known in the art may be used to drive the bone spikes 60 into the vertebral body "VB". The clinician would next drive the threaded portion 240 of bone screw 200 into the vertebral body "VB", such that bone screw 200 passes through throughhole 40 of plate 20 until the head portion 220 of bone screw 200 is disposed within throughhole 40.

Once plate 20 and bone screw 200 are against the vertebral body "VB", if desired, compression may be performed at this point to obtain the bone on bone contact desired and any spaces may be packed with allograft, autograft, or any other fusion-promoting material known in the art.

Spinal rod 100 may be initially aligned and adjusted by the clinician as needed for the particular procedure. Next, spinal rod 100 is inserted into one of first or second slots 30, 32 of plate 20. In an embodiment of the present disclosure, two spinal rods 100 are provided and inserted in each respective first and second slot 30, 32, such that a two-rail construct may be assembled. Threaded portion 310 of set screw 300 is next engaged with the threaded lumen 260 of bone screw 200, such that the spinal stabilization construct 1 is assembled in the unlocked position. In the unlocked position, head portion 220 of bone screw 200 has the first diameter "$D_1$", diameter 44 of throughhole 40 is in the collapsed position, and the first and second slots 30, 32 have the initial diameter 36a. With plate 20 in the unlocked position, spinal rod 100 may be further adjusted and aligned as needed by the clinician.

Once final adjustments are made to spinal rod 100, set screw 300 may be incrementally advanced, such that head portion 220 of bone screw 200 engages slotted wall segments 50 thereby expanding throughhole 40 to the expanded state, which transitions the first and second slots 30, 32. Advancement of the set screw 30 transitions the throughhole 40 to the expanded configuration, thereby transitioning the slots 30, 32 to the reduced diameter 36b, respectively. With spinal rod 100 partially secured within plate 20 of spinal stabilization system 1, further adjustment of spinal rod 100 may be performed taking advantage of the mechanical advantage. Once final adjustments to spinal rod 100 are performed, set screw 300 is fully advanced, thereby fully securing spinal rod 100 in one of the first or second slots 30, 32 of plate 20.

In accordance with another embodiment of the present disclosure, the clinician may perform the method described above with a plurality of spinal rods 100, bone screws 200, set screw 300, and plates 20, implanted in sequence, such that spinal stabilization construct 1 can be assembled into a multi-plate construct spanning multiple vertebral bodies "VB". Where a multi-plate construct is assembled, a plurality of bone screws 200 are implanted, as described above, such that a respective plate 20 and a respective set screw 300 are assembled onto each respective bone screw 200 (as illustrated in FIG. 6). With each respective plate 20 in the unlocked position, spinal rod 100 may be easily adjusted and aligned such that spinal rod 100 spans multiple vertebral bodies "VB", and may be disposed in a respective first or second slot 30, 32 of each respective plate 20. It is further envisioned that the two-rail construct described above may be performed with respect to the multi-plate construct. Additionally, it is envisioned that a variety of spinal rods 100 may be provided each having a different diameter, shape, and/or material.

In accordance with another embodiment of the present disclosure, a method of stabilizing a spine using spinal stabilization system 500 will now be described with reference to FIGS. 7-12. The method of using spinal stabilization system 500 operates in a similar fashion as spinal stabilization system 1, and therefore, only the differences will be detailed and discussed below.

The clinician is provided with a plate 520 and a plurality of bone screws 600 and threaded nuts 700. Initially, the clinician may pre-drill a hole and/or implant a plurality of bone screws 600 in sequence into vertebral bodies "VB", such that the threaded post 610 and seat 620 of each respective bone screw 600 are disposed above, and proximal to, the respective vertebral body "VB". The clinician next positions plate 520 over the plurality of implanted bone screws 600, such that the distal surface 550 of plate 520 abuts seat 620 of each bone screw 600, and the threaded post 610 of each bone screw 600 extends through one of elongated slot 540*a*, 540*b* or throughhole 542. The threaded surface 710 of a threaded nut 700 from the plurality of threaded nuts 700 is then coupled to the threaded post 610 of each implanted bone screw 600, such that plate 520 is positioned therebetween. Lastly, the threaded nuts 700 are fully advanced such that plate 520 is secured to the plurality of implanted bone screws 610, and the outer diameter 720 of each threaded nut 700 is fully disposed within one of elongated slot 540*a*, 540*b* or throughhole 542.

In accordance with the present disclosure, a kit will be described with reference to FIGS. 1-12. The kit includes plate 20, bone screw 200, set screw 300, and spinal rod 100. Additionally, the kit may include a plurality of plates 20, bone screws 200, set screws 300, and/or spinal rods 100. Further, the kit may include a plurality of spinal rods 100, wherein a variety of diameters, shapes, and/or materials are provided. Alternatively, the kit may include plate 500, bone screw 600, and threaded nut 700, and/or a plurality thereof.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the claims of the present application and their legal equivalents, rather than by the examples given.

What is claimed is:

1. A spinal stabilization system comprising:
    a plate including a proximal surface and a distal surface, the plate defining a length between a medial end and a lateral end, a throughhole having a non-threaded inner surface extending between the proximal surface of the plate and the distal surface of the plate, and a slot defined in the proximal surface, the slot transverse to a longitudinal axis extending through the throughhole and laterally offset from the throughhole, the slot having an opening oriented towards the proximal surface of the plate and a diameter that is adjustable between an initial configuration and a reduced configuration, the plate tapering along the length from the throughhole toward the medial and lateral ends;
    a bone screw including a head portion positionable within the throughhole of the plate and a threaded portion extending distally from the head portion, the threaded portion configured to secure the bone screw to a bone;
    a spinal rod positionable within the slot of the plate; and
    a locking member including a head section extending from a proximal surface of the locking member and a threaded section extending from a distal surface of the locking member with a non-threaded body section therebetween, the body section having a uniform diameter that is less than a diameter of the head portion, the locking member movable along the longitudinal axis of the throughhole and relative to the plate such that when the threaded section and the body section are advanced into the head portion and the head section is outside the head portion the diameter of the slot is in the initial configuration, and further advancement of the head section towards the distal surface of the plate reduces the diameter of the slot from the initial configuration to the reduced configuration, wherein when the diameter of the slot is in the reduced configuration, the head portion of the bone screw contacts the head section and the plate, wherein when the locking member is fully advanced into the throughhole, the proximal surface of the locking member is substantially flush with a proximal face of the bone screw.

2. The spinal stabilization system of claim 1, wherein a shoulder extends into the slot of the plate such that when the slot transitions from the initial configuration to the reduced configuration, the shoulder contacts a portion of the spinal rod disposed within the slot and exerts a compressive force thereon to secure the spinal rod within the slot.

3. The spinal stabilization system of claim 1, wherein the plate includes a bone spike extending from the distal surface of the plate.

4. The spinal stabilization system of claim 1, wherein the distal surface of the plate is arcuate.

5. The spinal stabilization system of claim 1, wherein the locking member is movable relative to the plate such that the proximal surface of the plate and athe proximal surface of the locking member are coplanar in the reduced configuration of the slot.

6. The spinal stabilization system of claim 1, wherein the head portion of the bone screw includes longitudinally extending segments radially disposed around a central opening of the head portion, the longitudinally extending segments flexibly transitionable between a first diameter and a second diameter which is larger than the first diameter.

7. The spinal stabilization system of claim 6, wherein the locking member is insertable into the central opening of the head portion of the bone screw such that advancement of the locking member into the head portion transitions the head portion from the first diameter to the second diameter and transitions the slot from the initial configuration to the reduced configuration.

8. The spinal stabilization system of claim 6, wherein the bone screw further includes a threaded lumen.

9. The spinal stabilization system of claim 8, wherein the threaded section of the locking member engages with the threaded lumen of the bone screw.

10. The spinal stabilization system of claim 6, wherein the longitudinally extending segments of the head portion of the bone screw are coupled to, and extend proximally from, the threaded portion of the bone screw.

11. The spinal stabilization system of claim 1, wherein the plate further includes flexible segments radially disposed about the throughhole, the flexible segments transitionable between collapsed and expanded configurations.

12. The spinal stabilization system of claim 1, further including a second spinal rod and the plate further includes a second slot, the second slot transverse to the longitudinal axis extending through the throughhole of the plate, the second spinal rod positionable within the second slot.

13. The spinal stabilization system of claim 1, wherein the locking member is moveable into the throughhole of the plate and is spaced from the non-threaded inner surface of the throughhole when the slot is in the reduced configuration.

14. A method of stabilizing a spine comprising:
positioning a distal surface of a plate adjacent a vertebral body, the plate defining a length between a medial end and a lateral end, the plate including a throughhole having a non-threaded inner surface extending between the distal surface of the plate and a proximal surface of the plate and a slot defined in the proximal surface of the plate, the slot transverse to a longitudinal axis extending through the throughhole and laterally offset from the throughhole, the slot having an opening oriented towards the proximal surface of the plate and a diameter that is adjustable between an initial configuration and a reduced configuration, the plate tapering along the length from the throughhole toward the medial and lateral ends;
driving a threaded portion of a bone screw into the vertebral body;
positioning a head portion of the bone screw in the throughhole of the plate;
placing a spinal rod into the slot of the plate;
advancing a head section of a locking member along the longitudinal axis of the throughhole and towards the distal surface of the plate to reduce the diameter of the slot from the initial configuration to the reduced configuration to secure the spinal rod in the slot, the head section extending from a proximal surface of the locking member, the locking member including a threaded section extending from a distal surface of the locking member with a non-threaded body section located between the head section and the threaded section, the body section having a uniform diameter less than a diameter of the head portion, wherein when the diameter of the slot is in the reduced configuration, the head portion of the bone screw contacts the head section and the plate, and when the threaded section and the body section are advanced into the head portion and the head section is outside the head portion the diameter of the slot is in the initial configuration, wherein when the locking member is fully advanced into the throughhole, the proximal surface of the locking member is substantially flush with a proximal face of the bone screw.

15. The method of claim 14, wherein positioning the distal surface of the plate adjacent the vertebral body further includes driving a bone spike extending from the distal surface of the plate into the vertebral body.

16. The method of claim 14, wherein advancing the locking member further includes incrementally advancing the locking member towards the distal surface of the plate and realigning the spinal rod during the advancement of the locking member.

17. The method of claim 14, further including:
positioning a second plate adjacent a vertebral body; and
securing the spinal rod within a slot of the second plate such that the spinal rod spans multiple vertebral bodies.

18. The method of claim 14, wherein advancing the locking member further includes moving the locking member into a central opening of the head portion of the bone screw, the head portion of the bone screw including longitudinally extending segments radially disposed around the central opening and flexibly transitionable between a first diameter and a second diameter which is larger than the first diameter such that advancement of the locking member into the head portion transitions the head portion from the first diameter towards the second diameter and transitions the slot from the initial configuration to the reduced configuration.

19. The method of claim 14, further including:
placing a second spinal rod into a second slot of the plate, wherein advancing the locking member also reduces a diameter of the second slot to secure the second spinal rod in the second slot.

* * * * *